United States Patent [19]

Peglion et al.

[11] Patent Number: 4,851,429
[45] Date of Patent: Jul. 25, 1989

[54] PHARMACEUTICALLY USEFUL TRICYCLIC AMINES DERIVED FROM 2,3,5,6,7,8-HEXAHYDRONAPHTHO(2,3-B)FURAN AND FROM 2,3,6,7,8,9-HEXAHYDRO-5H-BENZOCY-CLOHEPTA(2,3-B)FURAN

[75] Inventors: Jean L. Peglion, Les Vesinet; Jean C. Poignant, Bures S/Yvette; Joel Vian, Chaville, all of France

[73] Assignee: Adir et Cie, Neuilly-sur-Seine, France

[21] Appl. No.: 173,286

[22] Filed: Mar. 25, 1988

[30] Foreign Application Priority Data

Apr. 1, 1987 [FR] France ................. 87 04550

[51] Int. Cl.[4] ............ A61K 31/38; A61K 31/34; C07D 307/92; C07D 330/20
[52] U.S. Cl. ................. 514/444; 514/468; 549/60; 549/458
[58] Field of Search ............. 549/458, 60; 514/468, 514/444

[56] References Cited

U.S. PATENT DOCUMENTS 4,105,785  8/1978  Mauvernay et al. .......... 549/458

Primary Examiner—Mary C. Lee
Assistant Examiner—Bernard I. Dentz
Attorney, Agent, or Firm—Gordon W. Hueschen

[57] ABSTRACT

Compound of general formula I

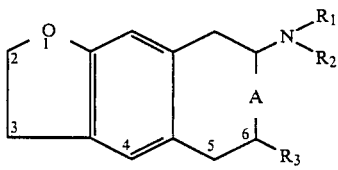

in which $R_1$ and $R_2$, which may be identical or different, each denote a hydrogen atom, a benzyl radical, a cyclohexylmethyl radical or a linear or branched alkyl radical containing from 1 to 10 carbon atoms, optionally substituted with a hydroxy radical, with a carboxy radical or with an alkoxy radical having 1 to 5 carbon atoms, with an alkoxycarbonyl radical having 2 to 6 carbon atoms, with an alkylphenyl radical having 7 to 16 carbon atoms or with a 2-alkylthienyl radical having 5 to 14 carbon atoms, $R_3$ denotes a hydrogen atom or a linear or branched alkyl radical containing from 1 to 4 carbon atoms, A denotes a single bond or a methylene radical, or a radical of formula

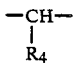

in which $R_4$ is a linear or branched alkyl radical containing from 1 to 4 carbon atoms.

These products are useful in anti-depressant, anti-aggressive, or dopaminergic modulation therapy and the corresponding bicyclic compounds are useful as intermediates for ring closure and production of the tricyclic compounds having the foregoing formula.

6 Claims, No Drawings

PHARMACEUTICALLY USEFUL TRICYCLIC AMINES DERIVED FROM 2,3,5,6,7,8-HEXAHYDRONAPHTHO(2,3-B)FURAN AND FROM 2,3,6,7,8,9-HEXAHYDRO-5H-BENZOCYCLOHEPTA(2,3-B)FURAN

The present invention relates to new tricyclic amines derived from 2,3,5,6,7,8-hexahydronaphtho[2,3-b]furan and from 2,3,6,7,8,9-hexahydro-5H-benzocyclohepta[2,3-b]furan, the processes for preparing them and the pharmaceutical compositions which contain them.

Some pharmacologically active tricyclic compounds derived from aminotetrahydronaphthalene are known. In effect, a few compounds of 7,8,9,10-tetrahydrobenzo[h]quinol-9-ylamine, whose antidepressant activity has been assessed only by in vitro tests, are mentioned in the literature (U.S. Pat. No. 4,521,423). 6,7,8,9-Tetrahydrobenzo[g]indol-8-ylamines and 6,7,8,9-tetrahydronaphtho[1,2-b]furan-8-ylamines endowed with dopaminergic stimulatory activity are described in U.S. Pat. Nos. 4,510,157 and 4,470,990.

The Applicant has now discovered that some tricyclic amines derived from 2,3,5,7,8-hexahydronaphtho[2,3-b]furan or from 2,3,6,7,8,9-hexahydro-5H-benzocyclohepta[2,3,-b]furan of novel structure possess very advantageous pharmacological properties. In effect, the compounds of the present invention possess dopaminergic properties and considerable antidepressant, antiaggressive and psychostimulatory activity, demonstrated by in vivo trials.

The subject of the present invention is, more especially, the compounds of general formula I

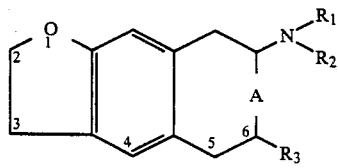

in which, $R_1$ and $R_2$, which may be identical or different, each denote a hydrogen atom, a benzyl radical, a cyclohexylmethyl radical or a linear or branched alkyl radical containing from 1 to 10 carbon atoms, optionally substituted with a hydroxy radical, with a carboxy radical or with an alkoxy radical having 1 to 5 carbon atoms, with an alkoxycarbonyl radical having 2 to 6 carbon atoms, with an alkylphenyl radical having 7 to 16 carbon atoms or with a 2-alkylthienyl radical having 5 to 14 carbon atoms, $R_3$ denotes a hydrogen atom or a linear or branched alkyl radical containing from 1 to 4 carbon atoms, A denotes a single bond or a methylene radical, or a radical of formula

in which $R_4$ is a linear or branched alkyl radical containing from 1 to 4 carbon atoms, in racemic form or in the form of optical isomers, and their addition salts with a pharmaceutically acceptable inorganic or organic acid.

The subject of the present invention is also the process for preparing the compounds of general formula I, wherein 2,3-dihydrobenzofuran of formula II

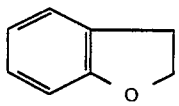

is condensed in the presence of a chlorinated organic solvent and aluminum chloride with an aspartic or glutamic anhydride derivative of general formula III

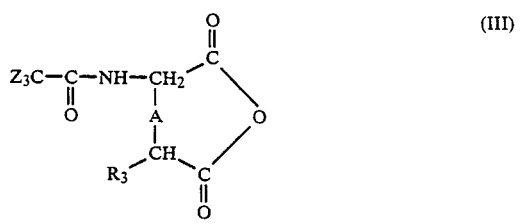

in which the meaning of A and $R_3$ is identical to that given for the formula I and Z denotes a hydrogen or fluorine atom, to form the compounds of general formula IV

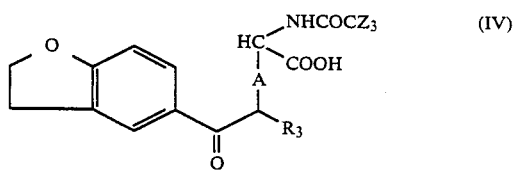

in which $R_3$, A and Z have the meaning stated above, which is reduced in the heated state with triethylsilane in the presence of trifluoroacetic acid to form the compounds of general formula V

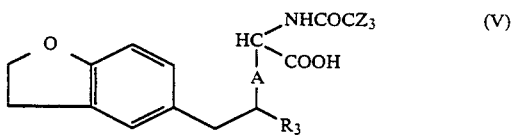

in which $R_3$, A and Z have the meaning stated above, which is subjected in the heated state to the action of phosphorus pentoxide in the presence of phosphoric acid to form the compounds of general formula VI

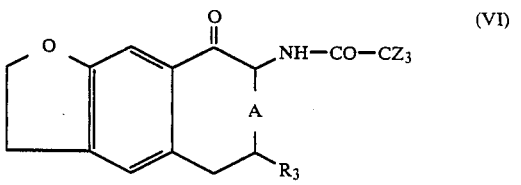

in which the meaning of $R_3$, Z and A is that stated above, which is subjected to a catalytic hydrogenation at room temperature in acid medium and in the presence of palladium on charcoal (5% palladium) to obtain an amide of general formula VII

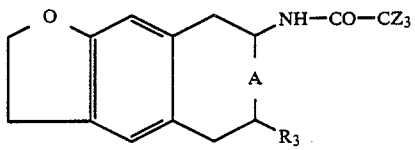

in which $R_3$, A and Z have the meaning stated above, which is reacted with a strong base to obtain a compound of general formula I in which $R_1$ and $R_2$ are identical and each denote a hydrogen atom, which then can be alkylated to form the corresponding secondary or tertiary amines, either by condensing it with a compound of general formula VIII

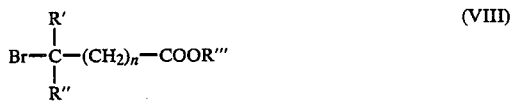

in which R' and R", which may be identical or different, each denote a hydrogen atom or lower alkyl radical having 1 to 4 carbon atoms, R''' denotes a lower alkyl radical having 1 to 5 carbon atoms and n is an integer from 0 to 9, to form a compound of general formula I in which $R_1$ denotes a hydrogen atom and $R_2$ denotes a linear or branched alkyl radical containing from 1 to 10 carbon atoms, substituted with an alkoxycarbonyl radical having 2 to 6 carbon atoms, which can then be subjected to the action of a strong inorganic base to form a compound of general formula I in which $R_1$ denotes a hydrogen and $R_2$ denotes a linear or branched alkyl radical having 1 to 10 carbon atoms, substituted with a carboxy radical, or by reacting it with an acid chloride of general formula IX $$W(CH_2)_nCOCl \qquad (IX)$$

in which n is an integer from 0 to 9 and W denotes a phenyl radical or a 2-thienyl radical, and then reducing the compound resulting from this reaction with a double metal hydride to form a compound of general formula I in which $R_1$ denotes an alkyl radical having 1 to 10 carbon atoms, substituted with a phenyl radical or a 2-thienyl radical, and $R_2$ is a hydrogen, or by reacting it with an appropriate quantity of formaldehyde and formic acid to obtain the compounds of general formula I in which $R_3$ and $R_4$ are identical and each denote a methyl radical, or by reacting it with an alkyl iodide of general formula X $$IR \qquad (X)$$

in which R denotes a linear or branched alkyl radical containing from 1 to 10 carbon atoms (optionally substituted with a hydroxy radical or with an alkoxy radical having 1 to 5 carbon atoms, or a cyclohexylmethyl radical, in the heated state in an organic solvent in the presence of an inorganic base, to form the compounds of general formula I in which $R_1$ and $R_2$ are identical and have the same meaning as R, or by subjecting it to the action of benzaldehyde in the heated state and in the presence of low molecular weight alcohol to form the corresponding benzylimine, and then to a catalytic hydrogenation followed by the action of formic acid and formaldehyde to form the compounds of general formula I in which $R_1$ denotes a methyl radical and $R_2$ a cyclohexylmethyl radical, or by subjecting it first to the action of benzaldehyde in the presence of an inert and apolar aromatic solvent and then, after removal of the solvent used, to the action of sodium borohydride in the presence of a low molecular weight polar aliphatic alcohol, to obtain a compound of general formula I in which $R_1$ denotes a hydrogen and $R_2$ a benzyl radical, which then can be subjected:

either to the action of formaldehyde and formic acid to form the compounds of general formula I in which $R_1$ denotes a methyl radical and $R_2$ a benzyl radical, or to the action of an alkyl iodide of general formula X to form the compounds of general formula I in which $R_1$ has the same meaning as R and $R_2$ denotes a benzyl radical, which then can be subjected to a catalytic hydrogenation to form the compounds of general formula I in which $R_1$ has the meaning given above and $R_2$ denotes a hydrogen atom, which then can be subjected to the action of an alkyl iodide of general formula X to form the compounds of general formula I in which $R_1$ and $R_2$, which may be identical or different, each denote an alkyl radical containing from 1 to 10 carbon atoms (optionally substituted with a hydroxy radical or an alkoxy radical having 1 to 5 carbon atoms) or a cyclohexylmethyl radical, which can then, if so desired, be salified with a pharmaceutically acceptable inorganic or organic acid, or be separated into their optical isomers and then salified.

Different compounds of general formula III are obtained by reacting acetic anhydride or trifluoroacetic anhydride with aspartic or glutamic acid or their analogues substituted with an alkyl at the β- or γ-position. The reaction is carried out first at a temperature below zero, and then at a temperature of between 30° and 60° C., according to the method described by BARKER C. C. in J. Chem. Soc. (1953), p. 453.

The aspartic acid derivatives containing an alkyl chain at the beta-position are obtained according to the method described by DAKIN H. D. in J. Biol. Chem. (1941), 141, p. 945: 950.

The methods of synthesis of the glutamic acid derivatives substituted with an alkyl at the β- or γ-position are also known (Gershon H, Parmegiani R, Giannasio V and Krull J., J. Pharm. Scien., (1975), 64, No. 11, p. 1855-1858).

The compounds of general formula I can be separated into their optical isomers after forming the salts with d- and l-camphorsulfonic acids.

Among pharmaceutically acceptable acids for preparing the addition salts with the compounds of general formula I, hydrochloric, phosphoric, fumaric, citric, oxalic, sulfuric, tartaric, maleic, mandelic and methanesulfonic acids, and the like, may be mentioned.

The compounds according to the invention, as well as their salts and their optical isomers, are endowed with highly advantageous pharmacological properties.

In effect, in vivo pharmacological trials have shown that the compounds possess potent antidepressant, antiaggressive and psychostimulatory properties. These properties have been demonstrated by means of tests classically used in animals, enabling the activity in man to be predicted with very great accuracy ("Antidepressants: Neurochemical Behavioral and Clinical Perspectives" Enna S. J., Malick J., Richelson E., Raven Press Ed., 1981, N.Y. and "Industrial Pharmacology, Antidepressants II", Fielding Stuart, Harbans Lal, Futura Publishing Comp. Ed., 1975, N.Y.).

The antiaggressive effects of the compounds of the invention were investigated by two methods. The first permitted an assessment of the inhibition of aggressive behavior in previously isolated mice (Charpentier J. "Analysis and measurement of aggressive behavior in mice", Aggressive Behavior, Garattini S. and Sigg E. B. Ed., p. 86–100, Excerpta Medica Found. Amsterdam, 1969), and the second, the inhibition of aggression in isolated and bulbectomized rats (Karli P, Vergnes M., and Didiergeorges F, "Rat mouse interspecific aggressive behavior and its manipulation by brain ablation and by brain stimulation", Aggressive Behavior, Garattini S. and Sigg E. B. Ed., p 47–55, Excerpta Medica Found. Amsterdam, 1969).

The compounds of the invention inhibit isolation-induced aggression in mice and aggression in isolated, bulbectomized rats. The effective doses are between 3 and 5 mg.kg.$^{-1}$, administered intraperitoneally.

The antidepressant effects of the compounds of the invention were investigated, employing the methods of antagonism of reserpine-induced hypothermia and antagonism of the ponto-geniculo-occipital waves induced by the compound Ro4-1284 in cats.

The tests for assessing the antagonism of reserpine-induced hypothermia were carried out on Swiss CD male mice. After distribution of the animals into groups, reserpine was injected intraperitoneally at a dose of 2.5 mg.kg.$^{-1}$. Three hours later, the compounds of the vention were administered by the same route. The rectal temperature of the animals was measured 1 hour and 2 hours after the second treatment, and compared with the initial temperature of these same animals measured immediately before the administration of the compounds undergoing testing. As the measurement time 2 hours after the administration, the compounds of the invention, at a dose of 2.5 mg.kg$^{-1}$ i.p., antagonize the reserpine-induced hypothermia to the extent of approximately 60%.

For assessing the antagonism of the ponto-geniculo-occipital P.G.O. waves induced by Ro4-1284 in cats, the method described by Ruch-Monachon M. A., Jalfre M. and Haefely W. (Arch. Int. Pharm. Therap., (1976), 219, No. 2, p. 251–346) was used.

The compounds of the invention strongly antagonize the P.G.O. waves induced in cats by the compound Ro4-1284, which depletes cerebral monoamines. For some of the compounds of the invention subjected to this test, the (i.v.) effective doses inhibiting by 50% the P.G.O. wave ratio (ED$_{50}$) are of the order of 0.14 to 0.20 mg.kg$^{-1}$.

The results of the pharmacological studies demonstrated that the compounds of the invention have a dopaminergic action, and more especially a dopamine-stimulating activity. This activity was assessed by the test of drug discrimination in rats, the general principles of which are stated in "Drug discrimination, application in C.N.S. Pharmacology", F. Colpaert Ed., Elsevier Biomedical, 1982, Amsterdam. At a dose of 2.5 mg.kg$^{-1}$, administered intraperitoneally, the compounds of the invention behave like apomorphine in the drug discrimination test, which proves that they have a dopaminergic action of an agonist nature. This activity is more pronounced when dextrorotatory isomers of the compounds of the invention are used for the test. Recently, it has been found that, in Parkinson's disease, there is a dopamine depletion of the central gray nuclei of the extrapyramidal system. Thus, dopaminergic agonists, like the compounds of the present invention, can have very advantageous therapeutic effects for the symptomatic treatment of this disease (Burgers Medicinal Chemistry 4th Ed., Part III, p. 413–430, (1981) J. Wiley and Sons Ed.). Dopamine also exerts a potent restraining effect on the secretion of prolactin, a hormone whose principle action is the development and maintenance of lactogenesis. The compounds of the present invention can hence also be used for treating neuroendocrine disorders due to a dopaminergic deficiency, such as hyperprolactinemia and galactorrhea (The Pharmacological basis of Therapeutics, 7th Ed., p. 1374–1385), Goodman Gilman A. Ed., Macmillan Publish. Comp. NY).

The invention also encompasses the pharmaceutical compositions containing, as active principle, at least one compound of general formula I, one of its isomers or one of its salts with a pharmaceutically compatible inorganic or organic acid, in combination with one or more inert and suitable excipients.

The pharmaceutical compositions thereby obtained are advantageously presented in various forms such as, for example, tablets, dragees, gelatin capsules, sublingual tablets or other galenical preparations suitable for sublingual administration, suppositories, injectable solutions or solutions to be taken by mouth.

The dosage can vary widely according to the patient's age and weight, the nature and severity of the condition and also the administration route.

The preferred administration route is the oral or parenteral route.

Generally speaking, the unit dosage will range between 0.5 and 100 mg, and the daily dosage, usable in human therapy, between 10 and 100 mg.

The examples which follow, given without implied limitation, illustrate the invention.

The melting points are measured according to the micro-Kofler technique. The proton nuclear magnetic resonance (NMR) spectra were recorded at 60 MHz.

EXAMPLE 1

N-Trifluoroacetylaspartic anhydride 0.49 mole of aspartic acid is cooled to −10° C. and 1.23 mole of trifluoroacetic anhydride is added dropwise while the temperature is maintained at −10° C. The reaction mixture is allowed to return to room temperature and is brought gradually to reflux for 2 hours. It is cooled, stirred in the presence of hexane and filtered. The solid residue obtained is dried.

Yield: 99%

Melting point: 137°–138° C.

EXAMPLE 2 dl-7-Amino-2,3,5,6,7,8-hexahydronaphtho[2,3-b]furan

STAGE A 4-(2,3-Dihydro-5-benzofuranyl)-4-oxo-2-trifluoroacetamidobutanoic acid 0.1 mole of the compound obtained in Example 1 and 0.05 mole of aluminum chloride suspended in 100 ml of dichloroethane are added to a solution of 12 ml of dichloroethane containing 0.05 mole of 2,3-dihydrobenzofuran. The mixture is stirred for 36 hours at room temperature and then hydrolyzed with saturated ammonium chloride solution. The mixture is extracted with dichloromethane and the extract washed with water, dried over magnesium sulfate, filtered and concentrated to obtain the expected product.

Yield: 88%

Melting point: 160°–162° C.

STAGE B 4-(2,3-Dihydro-5-benzofuranyl)-2-trifluoroacetamidobutanoic acid 0.25 ml of triethylsilane is introduced into a solution of 97 ml of trifluoroacetic acid containing 0.063 mole of the compound obtained in the preceding stage. The reaction medium is brought to reflux for 2 hours and then poured onto ice. The mixture is extracted with ether. The organic phase is washed with water and then dried over anhydrous magnesium sulfate. It is concentrated under reduced pressure (0.5 mm/Hg). The residue is dried under vacuum over phosphorus pentoxide and potassium hydroxide. The product is crystallized in a mixture of chloroform, toluene and hexane (20:20:80 V/V) to obtain pure 4-(2,3-dihydro-5-benzofuranyl)-2-trifluoroacetamidobutanoic acid.

Yield: 82%

Melting point: 125° C.

STAGE C

7-Trifluoroacetamido-2,3,5,6,7,8-hexahydronaphtho[2,3-b]furan-8-one 712 g of phosphorus pentoxide are added to 456 ml of 80% strength phosphoric acid. After the mixture is heated for 2 hours at 100° C., the temperature is allowed to return to 60° C. and 0.09 mole of 4-(2,3-dihydro-5-benzofuranyl)-2-trifluoroacetamidobutanoic acid, obtained in the preceding stage, is added. The reaction medium is stirred vigorously for one hour, then cooled and poured into water containing ice. The mixture is extracted with ether. The organic phase is washed with 10% strength aqueous sodium bicarbonate solution and then with saturated sodium chloride solution. 7-Trifluoroacetamido-2,3,5,6,7,8-hexahydronaphtho[2,3-b]furan-8-one is obtained after drying the ether phase over anhydrous sodium sulfate and evaporation under reduced pressure. The compound is then recrystallized in acetonitrile.

Yield: 40%

Melting point: 208° C.

STAGE D

7-Trifluoroacetamido-2,3,5,6,7,8-hexahydronaphtho[2,3-b]furan

Approximately 0.07 mole of the compound obtained in the preceding stage is dissolved in a mixture of 100 ml of acetic acid and 2 ml of 70% strength perchloric acid. Reduction is performed under a pressure of 5 kg/cm² of hydrogen in the presence of 1 g of palladium on charcoal (5% palladium), and the mixture is then filtered and concentrated under reduced pressure. The residue is taken up with water. The aqueous phase is separated and the organic phase is dried over anhydrous magnesium sulfate and concentrated. The product is recrystallized in isopropyl ether to obtain pure 7-trifluoroacetamido-2,3,5,6,7,8-hexahydronaphtho[2,3-b]furan.

Yield: 55%

Melting point: 131° C.

STAGE E

The amide obtained in the preceding stage is brought to reflux for 18 hours with 25 ml of 4N hydrochloric acid. After being cooled, the reaction medium is alkalinized and extracted with dichloromethane. After drying and evaporation, 7-amino-2,3,5,6,7,8-hexahydronaphtho[2,3-b]furan is obtained.

Melting point: 60° C.

After the amine thereby obtained has been dissolved in ethyl acetate, an appropriate quantity of ethereal hydrogen chloride is added slowly and with stirring to obtain the corresponding hydrochloride.

Melting point: 275° C.

NMR spectrum (CDCl$_3$+DMSO-d$_6$): 1.7 to 3.7 ppm, m, 9H; 4.6 ppm, t, 2H; 6.5 ppm, m, 1H; 7 ppm, m, 1H; 8.65 ppm, 3H, exchangeable.

EXAMPLE 3

7-Amino-6-methyl-2,3,5,6,7,8-hexahydronaphtho[2,3-b]furan

This compound may be prepared according to the process described in Example 2, but using 3-methyl-N-trifluoroacetylaspartic anhydride in Stage A. The latter compound may be prepared according to the process described in Example 1. The preparation of the corresponding acid is described in J. Biol. Chem., (1941), 141, p. 945–950.

EXAMPLE 4

8-Amino-2,3,6,7,8,9-hexahydro-5H-benzocyclohepta[2,3-b]furan

This compound may be prepared according to the process described in Example 2, but using N-trifluoroacetylglutamic anhydride instead of N-trifluoroacetylaspartic anhydride in Stage A.

EXAMPLE 5

8-Amino-7-methyl-2,3,6,7,8,9-hexahydro-5H-benzocyclohepta[2,3-b]furan

This compound may be prepared from 3-methyl-N-trifluoroacetylglutamic anhydride and according to the process described in Example 2. The 3-methylglutamic acid needed for the synthesis of the abovementioned anhydride may be prepared according to the process described in J. Pharm. Scien., (1975), 64, No. 11, p. 1855–1858.

EXAMPLE 6

8-Amino-6-methyl-2,3,6,7,8,9-hexahydro-5H-benzocyclohepta[2,3-b]furan

This compound may be prepared by condensing 4-methyl-N-trifluoroacetylglutamic anhydride with 2,3-dihydrobenzofuran according to the process described in Example 2. The synthesis of 4-methylglutamic acid is known (J. Pharm. Scien., (1975), 64, No. 11, p. 1855–1858).

EXAMPLE 7 d-7-Amino-2,3,5,6,7,8-hexahydronaphtho[2,3-b]furan camphorsulfonate

This salt was obtained by reacting the compound of Example 2 with an equimolar quantity of d-camphorsulfonic acid. After two recrystallizations in ethanol followed by two recrystallizations in methanol, the salt is obtained optically pure.

(Estimation by HPLC: >99%
Melting point: 253°–261° C.
Rotatory power of a 0.5% strength solution in water:

| λnm | 23° C. [α] D |
|---|---|
| 589 | +41.3° |
| 578 | +43.3° |
| 546 | +51.1° |
| 436 | +105.6° |
| 365 | +235.0° |

EXAMPLE 8 l-7-Amino-2,3,5,6,7,8-hexahydronaphtho[2,3-b]furan camphorsulfonate

This compound was obtained according to the process described in Example 7, but using l-camphorsulfonic acid.

Melting point: 254°–265° C.
Rotatory power of a 0.5% strength solution in water:

| nm | 23° C. [α] D |
|---|---|
| 589 | −49.1° |
| 578 | −51.4° |
| 546 | −60.3° |
| 436 | −125.0° |
| 365 | −276.4° |

EXAMPLE 9 d-7-Amino-2,3,5,6,7,8-hexahydronaphtho[2,3-b]furan hydrochloride

The compound of Example 7 is dissolved in ethyl acetate and the medium is then alkalinized with sodium hydroxide. The organic phase is separated, dried over anhydrous sodium sulfate and evaporated. The oil obtained is taken up in acetonitrile, and a stoichiometric quantity of ethereal hydrogen chloride is then added, to obtain optically pure d-7-amino-2,3,5,6,7,8-hexahydronaphtho[2,3-b]furan hydrochloride.

Melting point: 261°–264° C.
Rotatory power of a 0.25% strength solution in DMSO:

| λnm | 23° C. [α] D |
|---|---|
| 589 | +86.4° |
| 578 | +90.4° |
| 546 | +104.4° |
| 436 | +191.6° |
| 365 | +350.2° |

EXAMPLE 10 l-7-Amino-2,3,5,6,7,8-hexahydronaphtho[2,3-b]furan hydrochloride

This compound was obtained from the compound of Example 8 and according to the process described in Example 9.

Melting point: 262°–264° C.
Rotatory power of a 0.25% strength solution in DMSO:

| λnm | 23° C. [α] D |
|---|---|
| 589 | −86.4° |
| 578 | −90.4° |
| 546 | −104.4° |
| 436 | −191.6° |
| 365 | −350.2° |

Pharmaceutical Preparation

EXAMPLE 11

Tablets containing a 25-mg dose of d-7-amino-2,3,5,6,7,8-hexahydronaphtho[2,3-b]furan hydrochloride d-7-Amino-2,3,5,6,7,8-hexahydronaphtho[2,3-b]furan hydrochloride: 25.00 g
wheat starch: 100.00 g
cornstarch: 80.00 g
magnesium stearate: 15.00 g
talc: 20.00 g
for 1,000 tablets containing 25 mg of active principle.

We claim:

1. A compound of formula I

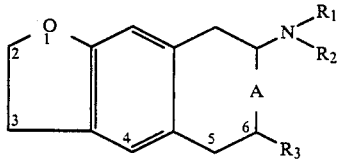

in which:

$R_1$ and $R_2$, which may be identical or different, each denote a hydrogen atom, a benzyl radical, a cyclohexylmethyl radical or a linear or branched alkyl radical containing from 1 to 10 carbon atoms, optionally substituted with a hydroxy radical, with a carboxy radical or with an alkoxy radical having 1 to 5 carbon atoms, with an alkoxycarbonyl radical having 2 to 6 carbon atoms, with an alkylphenyl radical having 7 to 16 carbon atoms or with a 2-alkylthienyl radical having 5 to 14 carbon atoms, $R_3$ denotes a hydrogen atom or a linear or branched alkyl radical containing from 1 to 4 carbon atoms, A denotes a single bond or a methylene radical, or a radical of formula

in which $R_4$ denotes a linear or branched alkyl radical containing from 1 to 4 carbon atoms, in racemic form or in the form of an optical isomer, or an addition salt thereof with a pharmaceutically acceptable inorganic or organic acid.

2. A compound of formula I as claimed in claim 1, in which A denotes a single bond.

3. A compound of formula I as claimed in claim 1, in which A denotes a methylene radical.

4. A pharmaceutical composition useful in treating a subject in need of antidepressant, antiaggressive, or dopaminergic modulation therapy containing, as active principle, an effective amount of a compound as claimed in claim 1.

5. The pharmaceutical composition as claimed in claim 4, containing the active principle at a dose of 0.5 to 100 mg.

6. The method of treating a subject in need of antidepressant, antiaggressive, or dopaminergic modulation therapy comprising the step of administering to the said subject an antidepressant, antiaggressive, or dopaminergic modulating amount of a compound of claim 1 or a pharmaceutical composition of claim 4.

* * * * *